United States Patent [19]

Fain et al.

[11] Patent Number: 5,693,081
[45] Date of Patent: *Dec. 2, 1997

[54] ENDOCARDIAL LEAD SYSTEM WITH DEFIBRILLATION ELECTRODE FIXATION

[75] Inventors: Eric S. Fain, Menlo Park; Drew A. Hoffman, Los Gatos; Benjamin D. Pless, Menlo Park, all of Calif.

[73] Assignee: Pacesetter, Inc., Sunnyvale, Calif.

[*] Notice: The term of this patent shall not extend beyond the expiration date of Pat. No. 5,476,500.

[21] Appl. No.: 540,864

[22] Filed: Oct. 11, 1995

Related U.S. Application Data

[63] Continuation of Ser. No. 170,133, Dec. 20, 1993, Pat. No. 5,476,500.

[51] Int. Cl.⁶ .................................................. A61N 1/05
[52] U.S. Cl. ........................................ 607/126; 128/642
[58] Field of Search .................................. 607/119, 122, 607/123, 126–131; 128/639, 642

[56] References Cited

U.S. PATENT DOCUMENTS

| | | | |
|---|---|---|---|
| Re. 30,366 | 8/1980 | Rasor et al. | 128/419 |
| 3,902,501 | 9/1975 | Citron et al. | 128/418 |
| 3,999,555 | 12/1976 | Person | 128/418 |
| 4,233,992 | 11/1980 | Bisping | 128/785 |
| 4,282,886 | 8/1981 | King | 128/785 |
| 4,289,144 | 9/1981 | Gilman | 607/128 |
| 4,402,329 | 9/1983 | Williams | 128/785 |
| 4,570,642 | 2/1986 | Kane et al. | 128/785 |
| 4,643,201 | 2/1987 | Stokes | 607/122 |
| 4,677,990 | 7/1987 | Neubauer | 128/786 |
| 4,827,940 | 5/1989 | Mayer et al. | 128/642 |
| 4,858,623 | 8/1989 | Bradshaw et al. | 128/785 |
| 4,945,922 | 8/1990 | Von Kreiken | 607/126 |
| 4,998,975 | 3/1991 | Cohen et al. | 128/419 |
| 5,016,808 | 5/1991 | Heil, Jr. et al. | 228/176 |
| 5,050,601 | 9/1991 | Kupersmith et al. | 607/126 |
| 5,052,407 | 10/1991 | Hauser et al. | 607/125 |
| 5,144,960 | 9/1992 | Mehra et al. | 607/125 |
| 5,174,289 | 12/1992 | Cohen | 128/419 |
| 5,314,462 | 5/1994 | Heil, Jr. et al. | 607/128 |
| 5,342,413 | 8/1994 | Hirschberg et al. | 607/126 |
| 5,405,374 | 4/1995 | Stein | 607/127 |
| 5,443,492 | 8/1995 | Stokes et al. | 607/131 |
| 5,476,500 | 12/1995 | Fain et al. | 607/126 |

FOREIGN PATENT DOCUMENTS

| | | |
|---|---|---|
| 2453840 | 5/1976 | Germany . |
| 8906148 | 7/1989 | WIPO . |

*Primary Examiner*—Lee S. Cohen
*Attorney, Agent, or Firm*—Steven M. Mitchell; M. Elizabeth Bush

[57] ABSTRACT

A lead system for use with an implantable cardioverter/defibrillator is disclosed. The lead system includes a fixation hook positioned approximately half-way between the distal tip of the lead and the tricuspid valve. The distal tip of the lead is positioned at the apex of the right ventricle and may or may not be secured there by a second fixation means such as a screw tip or tines. The fixation hook allows the defibrillation electrode to be accurately positioned by the patient's surgeon and maintained in contact with the septum wall of the patient's heart. By providing such intimate contact between the defibrillation electrode and the septum wall, defibrillation thresholds are reduced.

25 Claims, 5 Drawing Sheets

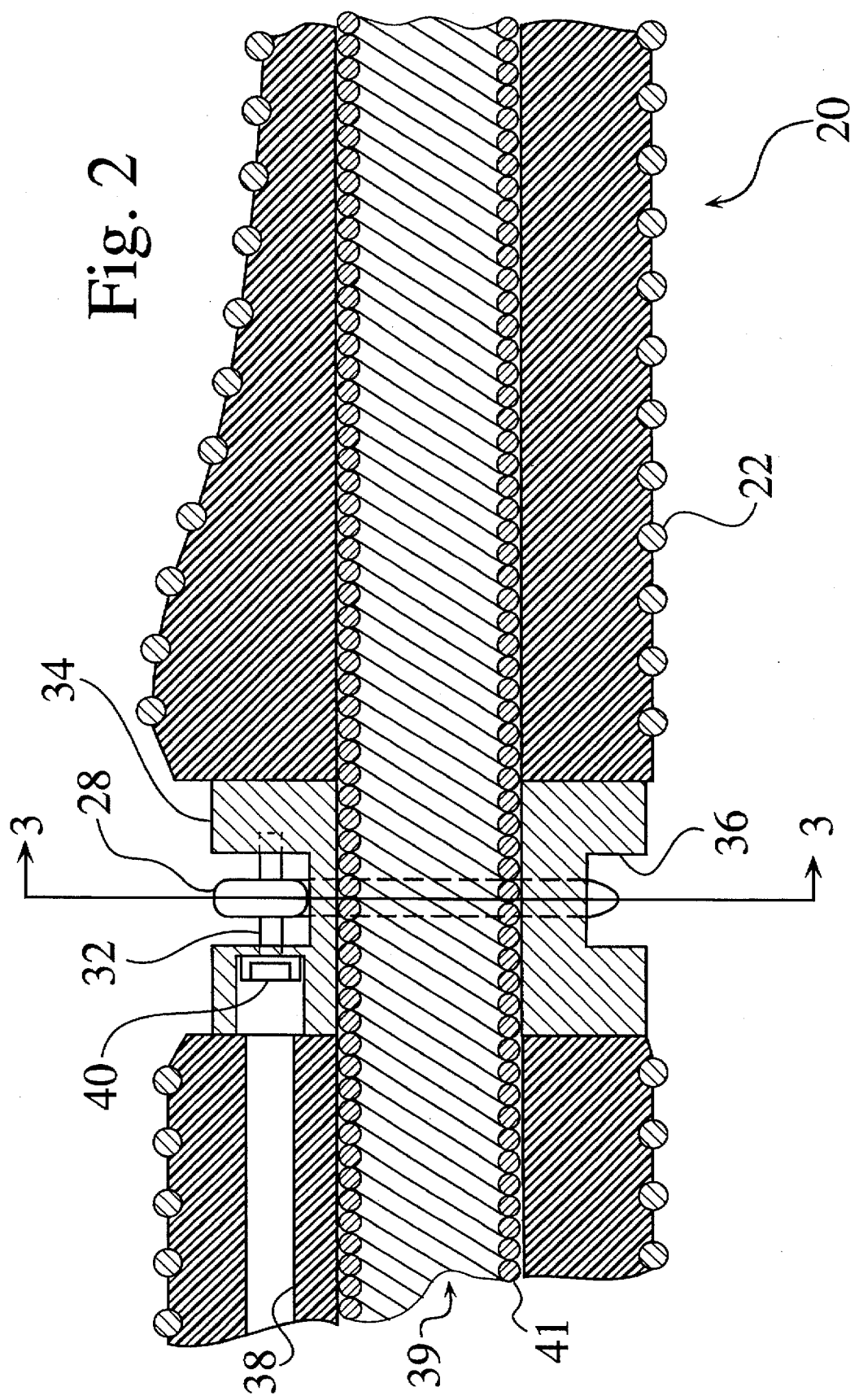

ENDOCARDIAL LEAD SYSTEM WITH DEFIBRILLATION ELECTRODE FIXATION

This is a continuation of application Ser. No. 08/170,133, filed on Dec. 20, 1993, now U.S. Pat. No. 5,476,500.

FIELD OF THE INVENTION

The present invention relates generally to lead systems for arrhythmia control devices, and more specifically to an endocardial lead system having a mechanism for fixation of the lead in the heart.

BACKGROUND OF THE INVENTION

The use of electrical signals to stimulate or steady heart rhythm (pacing) or to restore heart rhythm when the muscle fibers of the heart undergo very rapid irregular contractions, which result in very little pumping of blood (defibrillation), is a well accepted, lifesaving medical technique. Implantable cardioverter/defibrillator devices have been under development since at least the 1960's. The term cardioverter is used to mean a device for the correction of ventricular tachycardia (abnormally rapid heart rate of about 100-240 beats per minute) by discharging electrical energy into the heart. The term defibrillation is used to refer to high voltage shocks which terminate fibrillation (a rapid, chaotic heart rhythm resulting in no effective pumping of blood.) Implanted defibrillation is normally accomplished by passing a current between at least a pair of internally placed electrodes. The electrode arrangement may include a catheter or endocardial electrode which is transvenously positioned within the heart of the patient so that one of the electrodes is within the right ventricle. The other electrode, in the form of a flexible, substantially planar patch, is positioned outside the heart, either subcutaneously or within the thoracic cavity next to the left ventricle. Alternatively, the housing of the defibrillator may be used as an electrode. In other systems an electrode is positioned transvenously within the superior vena cava (SVC). The SVC electrode may be used in place of or in addition to the patch electrode. Electrical current is supplied to the electrodes by a battery powered pulse generator implanted under the skin of the patient, either in the abdominal or pectoral region. Improving the conductance path between the patch electrode (or device housing or SVC electrode) and the right ventricular (RV) electrode results in reduced energy required per defibrillation pulse and this may increase the lifetime of the system or allows for the use of smaller batteries.

For purposes of defibrillation, it is desirable to maximize the contact of the defibrillation electrode with the heart wall, preferably the septum between the right and left ventricles. Such intimate contact with the heart tissue makes defibrillation more effective by lowering the defibrillation threshold (DFT).

One prior art technique for positioning one or more defibrillation electrodes near the septum has used a lead system which includes a plurality of flexible electrodes which, when released, laterally expand into positions which bear resiliently against the surrounding heart walls. See PCT Application No. WO 89/06148 of Edhag. A similar system is disclosed in U.S. Pat. No. 4,998,975 to Cohen et al. These systems however, are somewhat complex and may be difficult to remove after chronic use. Additionally, the systems do not allow significant control in the placement of the electrodes.

A number of techniques have been developed for fixation of the distal end of transvenous endocardial leads within the heart of a patient. One such endocardial electrode is described in U.S. Pat. No. 3,902,501 to Citron et al. which uses a plurality of pliant fixation tines which extend at an acute angle to the lead body from the distal tip of the lead. When the lead is extended into the right ventricle, the tines act as an anchor catching in the trabeculae of the heart wall. Over time, the growth of tissue around the tines will further act to secure the lead tip in place. Another common prior art technique for lead fixation uses a helical or "screw" tip fixation device which extends from the distal tip of the lead body. A stylet or other mechanical means extending through the lead body is used to rotate the screw tip to cause it to bore into the heart tissue. Another fixation technique for a pacemaker lead is disclosed in U.S. Pat. No. 4,858,623 to Bradshaw et al. A rigid hook for engaging tissue is pivotally fastened to the lead in the vicinity of the electrode. The tip of the hook is normally resiliently urged into a recess in the lead adjacent to the electrode. A mechanism is coupled to the lead to permit the normal bias on the hook tip to be overcome to cause the hook to extend outward from the electrode. Each of these techniques is used to affix the distal tip of the lead body to the tissue of a patient's heart. However, with each of these prior art techniques, the positioning of the lead body is not accurately controlled, if at all.

Many of the prior art fixation techniques have been developed for use with pacemaker leads. With such leads, positioning of the distal tip of the lead is all that is required since the lead body is simply an insulated connector. Endocardial defibrillation leads, however, include a defibrillation electrode which extends along the lead body. Typically, the electrode of such prior art leads is fixated chronically by fibrosis or not at all and its placement is not accurately controlled at the time of implant.

It is an object of the invention to provide a transvenous lead system for use with an implantable cardioverter/defibrillator which allows precise electrode placement in intimate contact with the heart wall.

It is another object of the invention to provide a lead system having a fixation lumen for actuating a lead fixation device.

Other objects of the present invention will be apparent from the following description of the invention, read in connection with the drawings.

SUMMARY OF THE INVENTION

The present invention provides a novel transvenous lead system which allows precise placement of the defibrillation electrode along the heart wall. This is accomplished by providing a fixation device spaced along the length of the lead body for securing the electrode to the heart wall, preferably the septum between the right and left ventricle. The lead system includes a lead body with a proximal end for connection to an implantable cardioverter/defibrillator and a distal end for transvenous insertion into the right ventricle of a patient's heart. The distal tip of the lead is usually positioned in the apex of the right ventricle and may include fixation means such as a screw tip or tines. A defibrillation electrode begins near the distal tip and runs back along the length of the lead body. A fixation device is spaced along this portion of the lead body approximately half-way between the apex and the tricuspid valve. In a preferred embodiment, the fixation device comprises a fixation hook which is rotated out from the lead body for deployment and then counter rotated to pierce myocardial tissue and cause the lead body to be secured against the septum. The fixation hook is initially in a retracted position within a recess in the lead body to provide ease of insertion of the lead body through a vein into the heart. The hook may have either a circular or elliptical or other appropriate cross section. This embodiment facilitates explant of the lead system since the fixation hook may be rotated out of the septum and then back into the recess for removal. In the preferred embodiment, the lead body includes a fixation lumen which extends along a portion of the lead body parallel to the central lumen of the lead. A fixation stylet is extended through the fixation lumen during implant and used to rotate the hook first away from the lead body and then into the heart tissue.

In an alternative embodiment of the invention, two fixation hooks, spaced along the defibrillation electrode, are used. This provides two points of fixation ensuring maximum electrode/tissue contact.

In another alternative embodiment of the invention, a guiding catheter is used for placement of the lead, thereby shielding venous tissue from potential damage caused by the fixation mechanism during implant. This shielding may alternatively be accomplished by encapsulating the fixation mechanism in a material such as mannitol which harmlessly dissolves following exposure to body fluids.

BRIEF DESCRIPTION OF THE DRAWINGS

The various features and advantages of the present invention may be more readily understood with reference to the following detailed description taken in conjunction with the accompanying drawings in which:

FIG. 2 shows a cross-sectional view of a portion of the lead shown in FIG. 1;

DETAILED DESCRIPTION OF THE INVENTION

Figure 1:
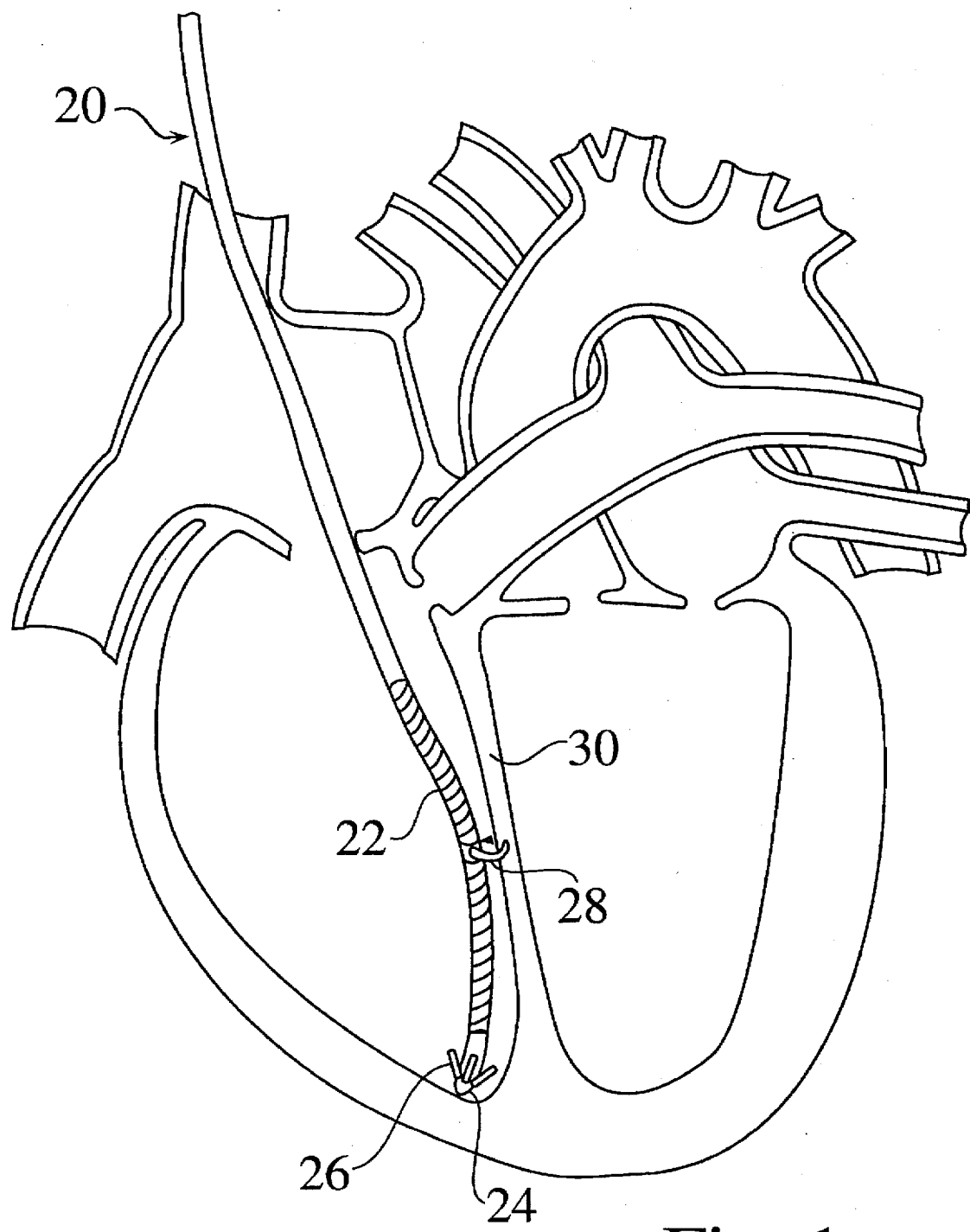
FIG. 1 shows a sectional view of a heart having a transvenous lead according to the invention inserted therein.

An endocardial lead system according to the invention will now be described with reference to FIGS. 1-5. An endocardial lead 20 shown in FIG. 1 includes a pacing/sensing tip 24 at the distal end and a defibrillation electrode 22 proximal of the distal end and extending along the lead body. The proximal end of lead 20 is connected to an implanted cardioverter/defibrillator (not shown) of known construction. The distal tip may include tines 26 to aid in fixation of the distal end within the apex of the patient's heart. In an alternative equally preferred embodiment, the distal fixation device may include a helical screw tip. In another alternative embodiment, the tip may include no fixation device at all. In such embodiment, the distal tip is retained in the apex region of the right ventricle by fixation of the lead body in the vicinity of the defibrillation electrode 22 to the ventricular septum wall 30 as described below.

FIG. 2 shows a portion of the lead 20 in cross-section which includes the defibrillation electrode 22 in the form of a conductive coil wound around the periphery of the lead body. The coil may be of the type disclosed in co-pending patent application Ser. No. 08/126,619 filed Sep. 24, 1993, which application is incorporated herein by reference. Other known electrode configurations may also be used. Coil 22 is connected to a lead conductor (not shown) at its distal and proximal ends. A fixation hook 28 is positioned in the region of the defibrillation electrode, preferably somewhere along its longitudinal extent. Hook 28 may have various cross sectional geometries including circular to provide a cylindrical hook body and rectangular to provide a flat, ribbon body. In either case, the hook is tapered to a sharp point at its tip. The ribbon configuration provides flexibility along the longitudinal extent of the lead and rigidity in the transverse plane. The hook 28 pivots on a pin 32 which is mounted in a fixation ring 34 within a recess 36. The hook 28 is typically a biocompatible metal such as MP35N or platinum/iridium and can either be active or passive, i.e. electrically connected to the defibrillation electrode 22 or not. Fixation ring 34 may be either conductive on non-conductive. It is important that the material of the hook not exhibit unwanted properties when exposed to high electric fields or currents while in the presence of body fluids. A fixation lumen 38 is provided along lead 20 parallel to and spaced from a lead central lumen 39. Central lumen 39 includes at least one conductor coil 41. Fixation lumen 38 extends along lead 20 to fixation ring 34. It can be open to body fluids if needed because it does not carry a lead conductor which would be susceptible to corrosion if exposed to body fluids. The proximal end of fixation lumen 38 extends to the venous insertion point, i.e. the point along the lead body where it first enters a vein.

Figure 3A:
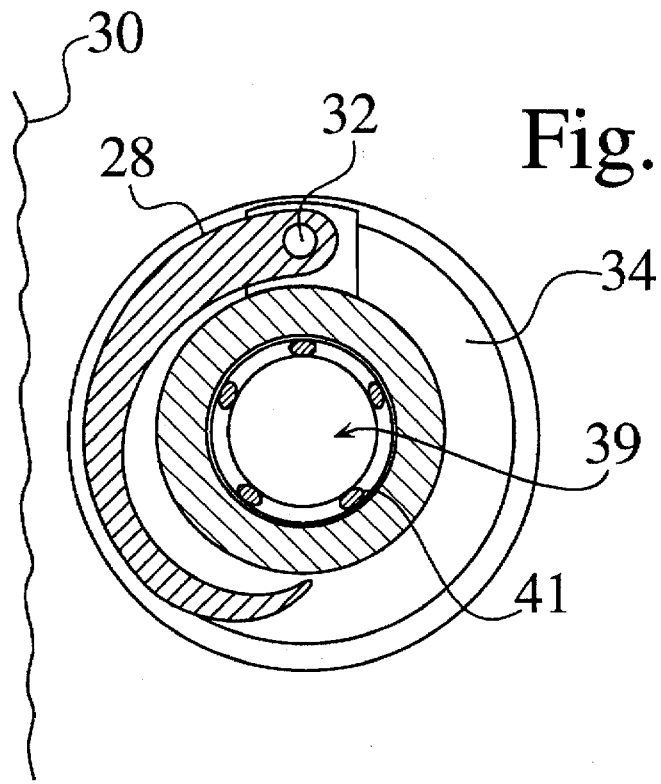
FIG. 3 shows a cross-sectional view of the lead of the invention along section 3—3 of FIG. 2.
FIG. 3B Shows the cross-section of FIG. 3A with the fixation hook deployed in the septum.
Figure 3B:
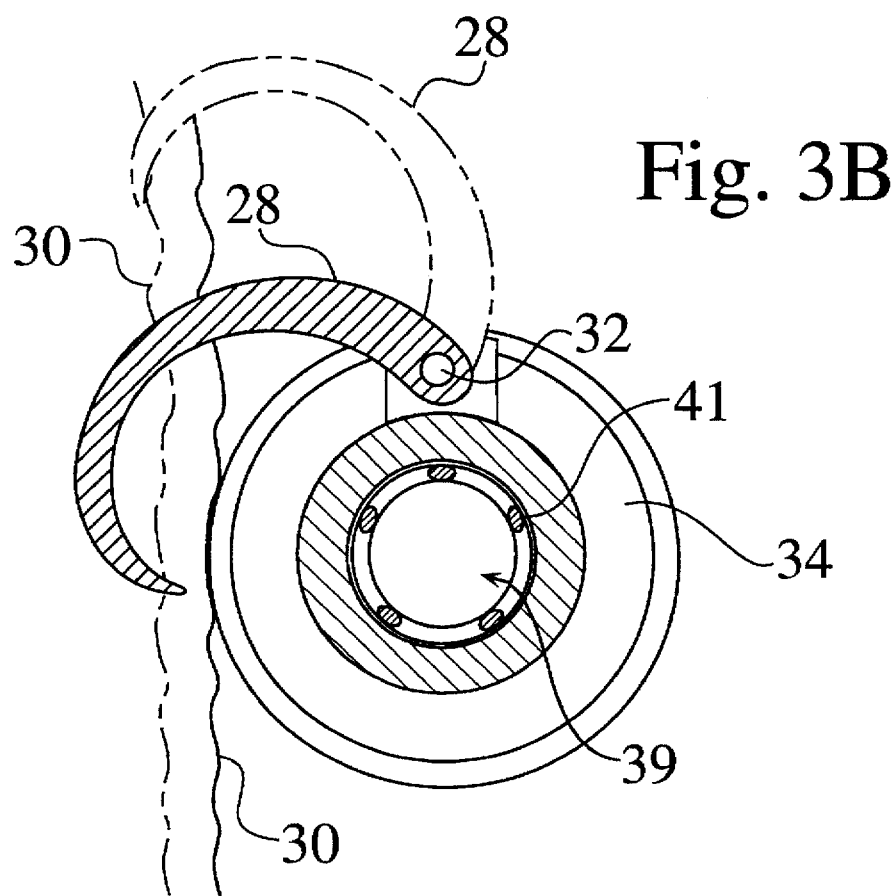

During implantation of the lead, hook 28 is retracted within recess 36 which extends around the periphery of fixation ring 34 as shown in FIGS. 2 and 3A. Once the distal end of lead 20 has been positioned within the right ventricle with the defibrillation electrode 22 proximate the septum 30, hook 28 is deployed by rotating it away from the lead body. This is accomplished using a fixation stylet which is inserted through fixation lumen 38. The styler has a slot head at its distal end which interfaces with a slot 40 in the head of pin 32. After the hook 28 is deployed away from fixation ring 34, it may be rotated in the opposite direction to pierce the myocardial tissue of the septum 30 to securely fix the defibrillation electrode 22 against the septum as shown in FIG. 3B. A depth of about one to three millimeters is sufficient to ensure fixation without any significant damage to the heart tissue. Attachment in this manner allows for later removal in the event this is so desired. The implanting surgeon will position the lead and actuate the fixation mechanism prior to tunneling the remainder of the lead to the pulse generator implanted in either the abdominal or pectoral region.

In an alternative embodiment, a similar fixation mechanism is used which does not include a fixation lumen but is actuated by a stylet passed down central tureen 39 of lead 20. In this embodiment, the stylet may extend through the fixation ring to the distal end of the lead to aid in positioning the lead adjacent the septum 30. The styler used for this embodiment has a flat section which mates with a slot in the supporting axis of hook 28. This embodiment presents a smaller lead cross section but the conductor and fixation mechanism must be constructed so as to prevent possible damage caused by their exposure to body fluids.

In another alternative embodiment of the invention, a second fixation ring may be used to provide attachment of the lead body to the septum at more than one location. This ensures improved contact at the defibrillation electrode/ tissue interface, thereby optimizing the reduction in defibrillation threshold.

In some embodiments of the invention, the hook may extend out from the lead body during implantation. In this case, as described above, the hook is flexible in the direction of the lead axis and is stiff in the transverse plane. This reduces the potential for damage of the blood vessels or heart valve during an implant or explant surgical procedure. Additionally, the lead can be rotated or "spun" in the reverse direction of the hook by the surgeon as the lead is being inserted to prevent the hook from catching on tissue. In such embodiment, the hook may be covered with a biocompatible material which is soluble in body fluids in a manner such as is described in U.S. Pat. No. 4,827,940 to Mayer et at., which patent is incorporated herein by reference. Mannitol or other sugars may be used. In this manner, the hook has a smooth coating during insertion of the lead thereby protecting the vein through which the lead is deployed. During and following insertion of the lead, the coating begins to dissolve and expose hook for the fixation step. Alternatively, the fixation mechanism may be shielded during the implantation procedure by using an insertion catheter in a known manner.

Figure 4:
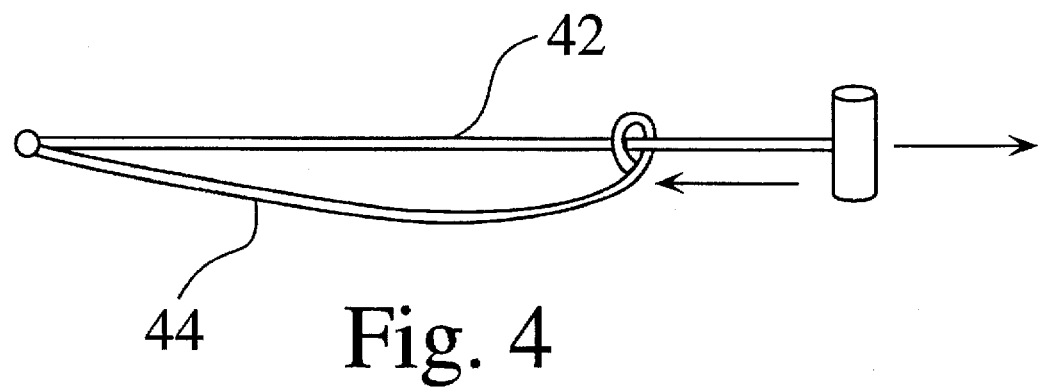
FIG. 4 is a diagrammatic representation of a bowing stylet used in positioning the lead of the invention.

One potential problem which may be experienced during implantation of the lead involves the step of positioning the defibrillation electrode against the septum prior to actuating the fixation hook. If this is a problem, a double, bowing stylet may be used to flex the electrode against the septum. FIG. 4 is a diagrammatic representation of such a stylet. Pulling on one arm 42 of the styler and pushing on the other arm 44 causes the pair to bow a sufficient amount to position the defibrillation electrode. Use of this technique for steerable guide wires is known in the art. Alternatively, a stylet may be shaped with an appropriate curvature or bend and then inserted into the central lumen of the lead body to position the fixation mechanism against the septum. Another technique for achieving the desired lead curvature is disclosed in U.S. Pat. No. 4,677,990 to Neubauer, which patent is incorporated herein by reference. A thread is anchored distally of the area of curvature and extends within the central lumen to the area of curvature. There the thread exits the central lumen and extends along the inside of an outer insulating sheath. The thread then reenters the central lumen and extends to the proximal end. By pulling on the thread, the lead is caused to curve in the area where the thread runs outside the central lumen.

In another alternative embodiment of the invention, a fixation device such as the one disclosed in U.S. Pat. No. 4,233,992 to Bisping, which patent is incorporated herein by reference, may be used to secure the defibrillation electrode to the septum. The fixation mechanism includes a spiral-shaped sharp fixing hook which may be provided with a spring winding. The hook is released once the lead body is in place and the spring action causes the hook to pierce the septum and fix the electrode thereto. As an alternative to using a spring to actuate the fixation hook, a stylet may be used to torque the spiral and "screw" it into the septum.

Figure 5:
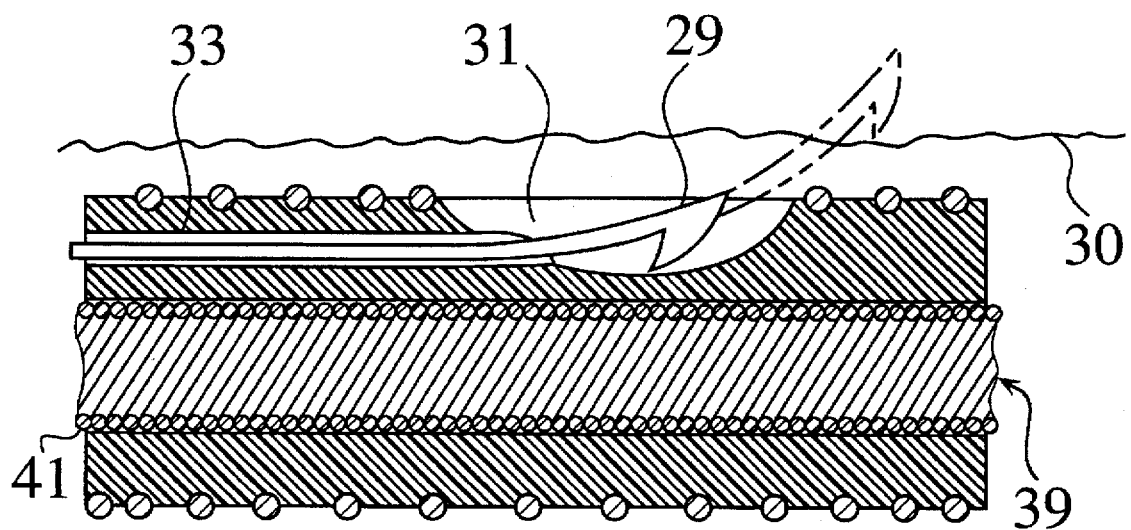
FIG. 5 is a cross-sectional view of a fixation ring of an alternative embodiment of the invention.

Another alternative embodiment of the invention is illustrated in FIG. 5. A fixation ring 34 is shown and is used with a lead having a fixation lumen such as is shown in FIG. 2. A barb 29 is positioned in a recess 31 during implantation. Once the electrode is positioned against the septum 30, a stylet 33 pushes the barb 29 out of recess 31 and causes it to pierce septum 30. A double bowing styler may be used to assist in positioning the defibrillation electrode 22 against the septum. Additionally, an insertion catheter or soluble coating may be used to shield the fixation mechanism during implantation as described above.

Figure 6:
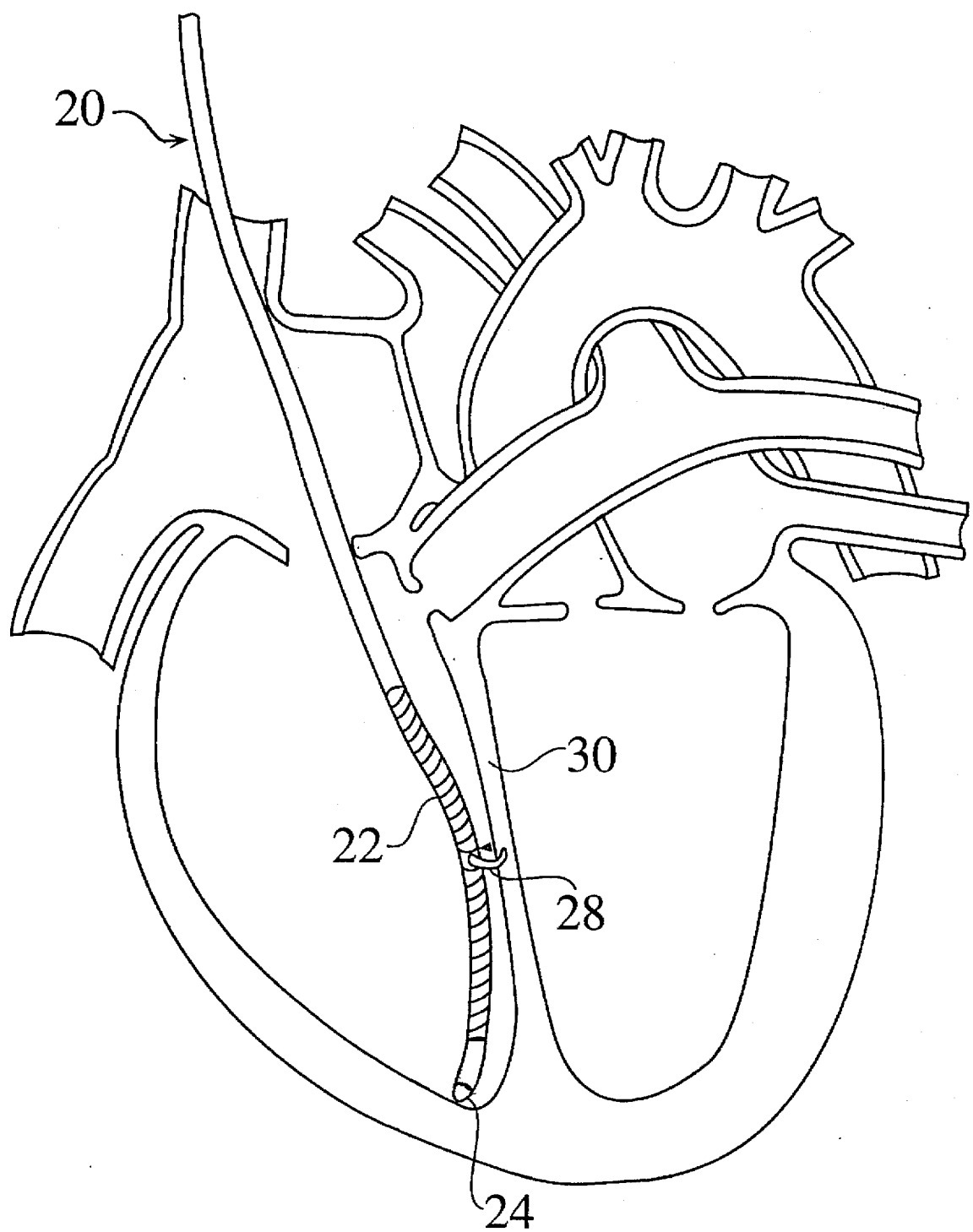
FIG. 6 illustrates a lead of the present invention having a distal tip having no fixation device.

FIG. 6 illustrates a lead of the present invention having a distal tip having no fixation device. The distal tip is retained in the apex region of the right ventricle by fixation of the lead body in the vicinity of the defibrillation electrode to the ventricular septum wall.

It should be understood that various alternatives to the embodiments of the invention described herein may be employed in practicing the invention. For example, the fixation means of the invention could be used to secure a lead body to other parts of the heart such as a wall of the right atrium to provide electrical stimulation to the atrium for atrial pacing or to treat atrial fibrillation. Additionally, a biocompatible adhesive could be used as the fixation means to secure the defibrillation electrode to the septum wall. It is intended that the following claims define the scope of the invention and that structures and methods within the scope of these claims and their equivalents be covered thereby.

What is claimed is:

1. An endocardial lead system comprising:
   a lead body having a distal end for positioning within a patient's heart and a proximal end for connection to a pulse generation device;
   a fixation device positioned on said lead body spaced from said distal end for securing said lead body to an interior wall of said patient's heart; and
   a defibrillation electrode on said lead body proximate said fixation device.

2. The lead system of claim 1 and further including means disposed at said distal end for securing said distal end to a separate portion of said patient's heart.

3. The lead system of claim 2 wherein said means disposed at the distal end of said lead body comprises a helical screw.

4. The lead system of claim 3 wherein said means disposed at the distal end of said lead body comprises a plurality of tines oriented at an acute angle along said lead body.

5. The lead system of claim 1 wherein said fixation device comprises a rigid curved hook secured to said lead body.

6. The lead system of claim 5 wherein said fixation device is initially encapsulated in a material which dissolves following exposure of the lead system to body fluids of said patient.

7. The lead system of claim 1 wherein said lead body includes a lumen extending therethrough and said lead body has a central axis, wherein said fixation device is laterally extensible from said lead body, said system further including a stylet for positioning within said lumen and having a distal end adapted to actuate said fixation device such that said fixation device is caused to extend laterally from said lead body into said portion of said patient's heart.

8. The lead system of claim 7 wherein said lumen is disposed along said central axis.

9. The lead system of claim 7 wherein said lumen is spaced radially from and parallel to said central axis.

10. The lead system of claim 1 wherein said lead body further includes a pacing/sensing electrode positioned at said distal end of said lead body.

11. The lead system of claim 1 wherein said fixation device is electrically connected to said defibrillation electrode.

12. The lead system of claim 1 wherein said fixation device includes at least two hooks spaced from each other along said lead body.

13. The lead system of claim 1 wherein said lead body includes a central lumen extending along the length of said lead body and a fixation lumen extending parallel to said central lumen along a portion of said lead body, said fixation lumen being adapted to receive a stylet for actuation of said fixation device.

14. The lead system of claim 1 and further including an insertion catheter for temporary use in transvenously positioning said lead body and for subsequent removal from said patient's body whereby said lead body is positioned within said catheter before or after insertion of said catheter in said patient's body.

15. The lead system of claim 1 wherein said fixation device comprises a spiral-shaped fixing hook.

16. The lead system of claim 1 wherein said fixation device comprises a biocompatible adhesive.

17. A method for implanting the lead of claim 1, comprising the steps of:
    (a) positioning said distal end in said patient's right ventricular apex; and
    (b) securing said lead body against said patient's septum using said fixation device.

18. An endocardial defibrillation lead comprising:
    a lead body having a distal end for positioning within a patient's heart and a proximal end for connection to an implantable pulse generator;
    a defibrillation electrode positioned on said lead body near said lead body distal end, said defibrillation electrode having distal and proximal ends; and
    a fixation device positioned on said lead body proximal of said distal end of said defibrillation electrode and capable of securing said lead body to an interior portion of said patient's heart.

19. The endocardial lead system of claim 18 wherein said lead body further includes a pacing/sensing tip electrode positioned distal of said defibrillation electrode.

20. The endocardial lead system of claim 18 and further including means disposed at said lead body distal end for securing said lead body distal end to a separate portion of said patient's heart.

21. The lead system of claim 20 wherein said means disposed at the distal end of said lead body comprises a helical screw.

22. The lead system of claim 20 wherein said means disposed at the distal end of said lead body comprises a plurality of tines oriented at an acute angle along said lead body.

23. The endocardial lead system of claim 19 wherein said pacing/sensing tip electrode is adapted to be retained in said patient's right ventricular apex region by fixation of said lead body in the vicinity of said defibrillation electrode to said patient's ventricular septum wall.

24. The endocardial lead system of claim 18 wherein said lead body distal end is adapted to be retained in said patient's right ventricular apex region by fixation of said lead body in the vicinity of said defibrillation electrode to said patient's ventricular septum wall.

25. A method for implanting the lead of claim 18, comprising the steps of:
    (a) positioning said lead body distal end in said patient's right ventricular apex; and
    (b) securing said lead body against said patient's septum using said fixation device.

* * * * *